United States Patent [19]

Morrow

[11] Patent Number: 5,004,338

[45] Date of Patent: Apr. 2, 1991

[54] METHOD AND APPARATUS FOR ATTENUATION AND MEASUREMENT OF LASER POWER AT THE END OF A LASER GUIDE

[76] Inventor: Clifford E. Morrow, 576 Hatchery Rd., North Kingstown, R.I. 02852

[21] Appl. No.: 317,575

[22] Filed: Mar. 1, 1989

[51] Int. Cl.$^5$ .................. G01J 1/04; A61B 17/36; B23K 26/02

[52] U.S. Cl. .................. 356/218; 219/121.61; 219/121.83; 606/11

[58] Field of Search .................. 356/73.1, 218, 225; 219/121.61, 121.83; 606/10, 11, 12

[56] References Cited

U.S. PATENT DOCUMENTS 4,459,986 7/1984 Karaki .................. 606/11
4,772,772 9/1988 Juptner et al. .................. 219/121.83

FOREIGN PATENT DOCUMENTS 57-19089 1/1984 Japan .................. 219/121.61

Primary Examiner—Vincent P. McGraw
Attorney, Agent, or Firm—Kenyon & Kenyon

[57] ABSTRACT

Laser power is delivered at normal intensities or powers to the end of a laser guide such as an articulated arm from a laser console where the beam enters an attached attenuating unit. Inside the attenuator, the beam encounters a dual wavelength beam splitter that transmits an attenuated beam at, for example, 20 times reduction of power. The attenuated beam may be delivered to an area of medical treatment. The beam splitter is also reflective and reflects the remaining power to a power sensor where the thermal energy is absorbed and measured. The power of the attenuated beam is related to the power of the measured reflected beam. The beam splitter is coated to allow maximum transmission of a visible guide beam that always travels coaxially to the operating laser energy being attenuated. A signal from the power sensor is provided to a preferably battery powered read-out device that provides the surgeon with real time accurate readings of delivered power.

18 Claims, 1 Drawing Sheet

METHOD AND APPARATUS FOR ATTENUATION AND MEASUREMENT OF LASER POWER AT THE END OF A LASER GUIDE

BACKGROUND OF THE INVENTION

The present invention relates to the attenuation and measurement of laser beam power. In particular, it relates to the attenuation and measurement of laser beam power at the end of a laser guide such as an articulated arm which is used for providing a laser beam to an area of medical or surgical treatment. Even more particularly, the present invention is directed to attenuating the laser beam power at the end of an articulated arm laser guide to the low power levels necessary for medical or surgical treatment while at the same time providing the ability to measure accurately the delivered laser power.

The present surgical technology, and in particular, $CO_2$ laser technology, uses an articulated arm to deliver spatially coherent light from a laser to a focusing accessory or other beam delivery device located at the end of the arm. Most often the laser is capable of delivering power in excess of 50 watts to the input end of the arm.

In general, the typical laser has a useful dynamic range of from 5:1 to 10:1. This limits the laser power to between 5 and 10 watts before instabilities occur that result in unstable power delivery.

Many surgical procedures must be performed in the power range of 20 milliwatts to 2 watts requiring some means of low power control. Current methods employ beam splitters within the laser console; however, this method results in inaccurate delivery of power since the power is measured before transmission through the arm. In addition, power measurement 29 devices designed to detect power at the 50 watt level are not accurate at 20 milliwatts.

The inventor is aware of the following references which relate to the measurement or detection of laser power levels.

| | |
|---|---|
| 4,459,986 - Karaki | 4,556,875 - Ishiwatari |
| 4,476,512 - Sunago et al | 4,716,288 - Doi |
| 4,711,526 - Hennings, et al | 4,423,726 - Imagawa et al |
| 4,564,012 - Shimada et al | 4,627,435 - Hoskin |
| 4,580,557 - Hertzmann | |

U.S. Pat. No. 4,459,986 to Karaki discloses a surgical laser system wherein an amount of energy of an output laser beam emanating from a distal end of a flexible light guide is measured by arranging a partial reflecting mirror having a reflection factor of about 99% and a transmissivity of about 1% at the last rotating joint portion of the light guide nearest to the distal end. A heat sink is applied onto a rear surface of the partial reflecting mirror and a thermocouple is arranged in contact with the heat sink to measure the temperature of the heat sink due to the transmitted energy. The output energy of the laser beam can be accurately measured by the thermocouple without being affected by a variation of the transmissivity of the light guide.

The '986 Karaki patent thus shows placement of a thermal sensor near the end of a light guide so that the amount of laser energy can be measured at the output. This reference does not, however, disclose or suggest the concept of attenuating the laser energy at the distal end of a laser guide so that low energy levels can be accurately delivered to the area of medical treatment.

U.S. Pat. No. 4,476,512 to Sunago et al is similar to the Karaki reference in that it discloses the use of a sensor element located near the distal end of a light fiber for monitoring the laser power at the distal end of the fiber. Again, however, there is no teaching or suggestion of attenuating laser power at the distal end of a light fiber.

U.S. Pat. No. 4,711,526 to Hennings, et al discloses an attenuating beam splitter. Two beams are produced by the beam splitter, a primary beam, and a secondary beam, the latter being a product of at least two internal reflections within the refractive element comprising the beam splitter. The secondary beam is used for aiming since the full power beam will travel along the same path as the attenuated beam after the refractive element is moved out of the path.

U.S. Pat. No. 4,564,012 to Shimada et al discloses a laser surgical device wherein a laser power meter is provided into which a laser handpiece is inserted in order to check if the output power of the laser coincides with the desired power setting.

U.S. Pat. No. 4,580,577 to Hertzmann is similar to the Shimada et al reference in that it discloses the use of a calibration pod for calibrating the output of the laser device.

U.S. Pat. No. 4,556,875 to Ishiwatari discloses a power monitoring system for an optical fiber wherein a light detector is disposed in a handpiece provided at the output end of the optical fiber.

U.S. Pat. No. 4,716,288 to Doi discloses a device for detecting defects in a transmitting fiber which operates on the principle of detecting the amount of light reflected from the exit face of the optical fiber.

U.S. Pat. No. 4,423,726 to Imagawa et al discloses a safety device for a laser ray guide in which a laser ray-receiving element is installed on the input side of a lens of a laser ray guide such that defects occurring in the laser ray guide can be detected by the energy reflected to the laser ray-receiving element.

U.S. Pat. No. 4,627,435 to Hoskin shows a surgical knife heated by a laser with a thermocouple disposed in the knife for control purposes.

SUMMARY OF THE INVENTION

It is an object of the present invention to provide a method and apparatus for accurately delivering low levels of laser power.

It is yet another object of the present invention to provide a method and apparatus for accurately delivering low levels of laser power to an area of medical or surgical treatment.

It is furthermore an object of the present invention to provide such a method and apparatus wherein a relatively high power laser beam is attenuated at the end of a laser guide such as an articulated arm to a low power beam.

It is yet still a further object of the present invention to measure the power level delivered to the area of medical treatment at the end of the articulated arm thereby providing for an accurate measurement of the power levels delivered.

It is yet still a further object of the present invention to provide such a method and apparatus for measuring the laser power delivered to an area of medical or surgical treatment wherein power levels in the milliwatt to low watt range, e.g., from 20 milliwatts to 2 watts, may be accurately measured.

The above and other objects of the present invention are achieved by an apparatus for providing accurate delivery and measurement of low levels of laser power at the end of a laser guide comprising a housing disposed at the end of the laser guide having an input and an output, the input receiving an input laser beam of a higher level of laser power than is provided at the output, a laser power level attenuation device disposed in the housing for attenuating the input beam and providing an attenuated output beam to the output, the attenuation device further providing a reflected beam, and a power sensor disposed in the housing receiving the reflected beam for measuring a power level of the reflected beam, thus providing a measurement related to the power level of the output beam, the power sensor further absorbing the energy of the reflected beam. A display device is coupled to the power sensor for providing a display of the power level of the output beam.

Since the procedures that require very low power levels, i.e., tissue welding, neurosurgery, microsurgery and others require very accurate knowledge of power level delivery with no variation or instability of the delivered beam, power measurement close to the surgical site in combination with attenuation of a more powerful stable beam of light provides a functional advantage over presently known methods and apparatus.

The invention provides that the laser power is delivered at normal intensities or powers to the end of the articulated arm from the laser console where the beam enters an attached attenuator unit. Inside the attenuator, the beam encounters a dual wavelength beam splitter that transmits an attenuated beam to the area of medical treatment at, for example, 20 times reduction of power. The beam splitter is also reflective and reflects the remaining power to a power sensor where the thermal energy is absorbed and measured. The body of the attenuator may be finned to help dissipate the accumulated heat of attenuation. The beam splitter may be coated to allow maximum transmission of the visible guide beam that always travels coaxial to the operating laser energy being attenuated.

The signal from the power sensor is preferably provided to a battery powered read-out that provides the surgeon with real time accurate readings of delivered power. The read-out preferably is battery powered to avoid the chance of ground leakage current to the attenuator that may be attached to surgical probes in contact with open tissue.

Preferably the invention also provides that the beam splitter be mounted at less than 15° to the normal. At angles greater than 15°, the reflective coating on the beam splitter will be sensitive to rotations of laser beam polarization that will result in power fluctuations and loss of accurate power readings.

BRIEF DESCRIPTION OF THE DRAWINGS

The invention will be explained in greater detail in the following detailed description with reference to the drawings in which.

DETAILED DESCRIPTION

Figure 1:
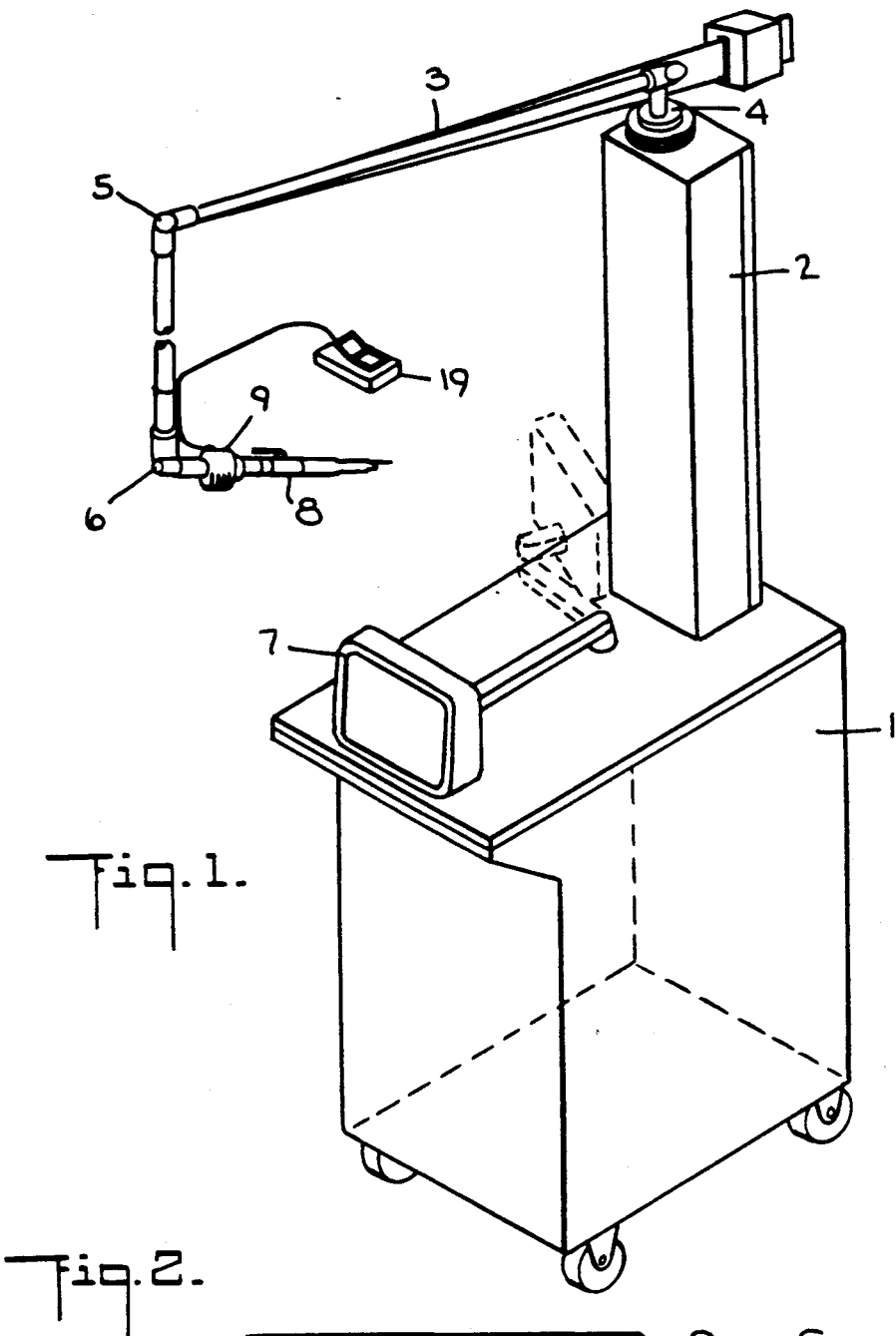
FIG. 1 shows an example of a medical laser treatment device wherein the output of the laser unit is supplied to an articulated arm for delivery to the area of surgical or medical treatment.

With reference to the drawings, FIG. 1 shows a medical laser treatment device comprising a laser console 1, for example, containing a $CO_2$ laser. The console is provided with a tower 2 through which the laser beam is supplied to an articulated arm 3. The articulated arm includes a plurality of joints 4, 5 and 6, which allow rotation about a plurality of axes and optical elements for suitably directing the laser beam along the arm. Additional joints may also be provided. The laser console may include a suitable display device 7 for displaying information to the operator. At the end of the articulated arm, a laser beam output device 8 is provided which includes an attenuator 9, which is shown in cross-section in greater detail in FIG. 2. A battery powered read-out device 19 may be provided to give the surgeon real time accurate readings of delivered power. The read-out is preferably battery powered to avoid the chance of ground leakage current to the attenuator 9 that may be attached to surgical probes in contact with open tissue.

Figure 2:
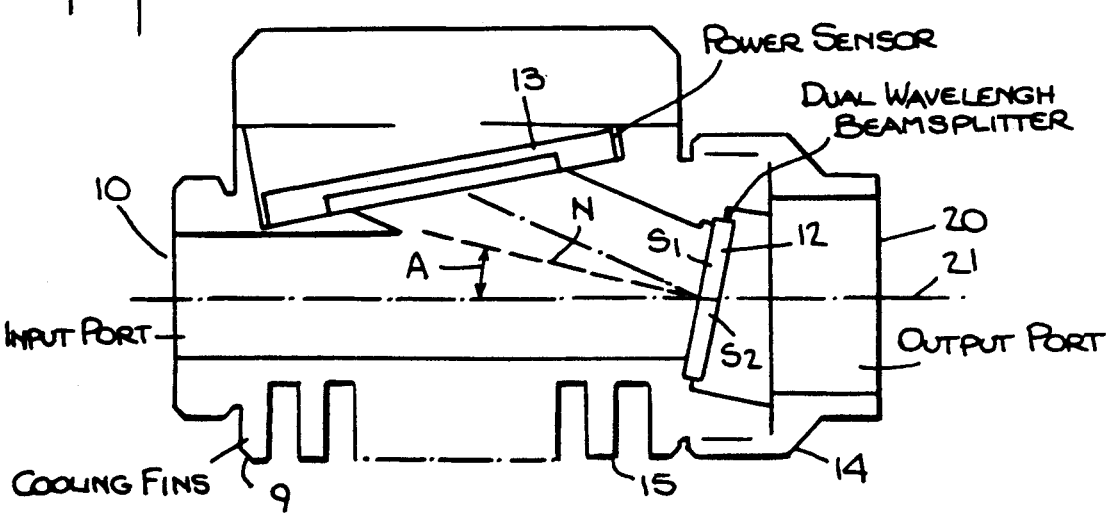
FIG. 2 shows the optical attenuator and measuring device located at the end of the articulated arm.

FIG. 2 shows, in cross-section, the optical attenuator 9 disposed at the end 8 of the articulated arm. The optical attenuator comprises an input port 10 and an output port 20. Laser energy from the articulated arm is delivered along the axis 11 to a beam splitter 12. The beam splitter 12 comprises a dual wavelength beam splitter that transmits an attenuated beam to the area of medical treatment at, for example, a 20 times reduction of power. The attenuated beam is shown at 21. The beam splitter 12 is also reflective and reflects the remaining power to a power sensor 13, which may comprise a thermal power sensor where the thermal energy is absorbed and measured. The body 14 of the attenuator may be suitably finned as at 15 to help dissipate the accumulated heat. The beam splitter 12 is also coated to allow maximum transmission of the visible guide beam that always travels coaxially with the working or operating, e.g. infrared, laser energy being attenuated. A signal from the power sensor 13 is provided to the battery powered read-out device 19 for display of accurate readings of delivered power.

Preferably the beam splitter 12 is mounted such that the normal N to the planar surface of the beam splitter is less than 15° to the longitudinal axis 11. At angles A greater than 15°, the reflective coating on the beam splitter 12 may be sensitive to rotations of laser beam polarization that will result in power fluctuations and loss of accurate power readings. In particular, it has been found that an angle of 12° between the normal to the beam splitter surface and the optical axis is preferable.

The characteristics of the beam splitter are preferably as follows. In an exemplary embodiment, the input side S1 is coated to have a reflectivity of 95%±1% and is planar (plano). At an input wavelength of 10.6 uM ($CO_2$ laser), it is preferably mounted such that the normal to its surface is 12° to the optical axis. The beam splitter should have minimum sensitivity to polarization changes, i.e., within ±1%.

The beam splitter should have maximum transmissivity for the visible guide beam used, e.g., for HeNe, at 0.6328 uM.

The output side S2 of the beam splitter should also be a planar (plano) surface, and be anti-reflection (AR) coated for the input wavelength, for $CO_2$ lasers, 10.6 um. The output surface should also be anti-reflection coated for the visible guide beam on a best efforts basis.

Both the input and output surfaces should be flat ($\lambda/2$) at 0.6328 uM (visible guide beam wavelength) and should have a wedge of less than one arc minute.

Preferably the beam splitter is made of zinc selenide (ZnSe) polycrystalline. A suitable beam splitter is available from II–VI, Inc., of Saxonburg, Pa.

Power sensor 13 may be a thermopile power detector available from Coherent, Inc., of the type disclosed in U.S. Pat. No. 3,596,514 or any other suitable device known to those skilled in the art.

In the foregoing specification, the invention has been described with reference to a specific exemplary embodiment thereof. It will, however, be evident that various modifications and changes may be made thereunto without departing from the broader spirit and scope of the invention as set forth in the appended claims. The specification and drawings are, accordingly, to be regarded in an illustrative rather than in a restrictive sense.

What is claimed is:

1. Apparatus for providing accurate delivery and measurement of low levels of laser power at the end of a laser guide comprising:
   a housing disposed at the end of the laser guide having an input and an output, said input receiving an input laser beam of a higher level of laser power than is provided at the output;
   a laser power level attenuation device disposed in the housing for attenuating the input beam and providing an attenuated output beam to the output, said attenuation device further providing a reflected beam, said attenuation device comprising a duel wavelength beam splitter for providing said attenuated output beam and reflecting said reflected beam and further for transmitting a visible guide beam for guiding an operator in the placement of the attenuated output beam; and
   a power sensor disposed in the housing receiving the reflected beam for measuring a power level of the reflected beam, thus providing a measurement related to the power level of the output beam, said power sensor further absorbing the energy of said reflected beam.

2. The apparatus recited in claim 1, further comprising a display device coupled to the power sensor for providing a display of the power level of the output beam.

3. The apparatus recited in claim 1, wherein the dual wavelength beam splitter is disposed at an angle to a longitudinal axis of the housing such that a normal to the plane of the beam splitter is at an angle of less than 15° with respect to the longitudinal axis.

4. The apparatus recited in claim 3, wherein said angle is 12°.

5. The apparatus recited in claim 2, wherein the display device is battery powered.

6. The apparatus recited in claim 1, wherein the laser guide comprises an articulated arm.

7. The apparatus recited in claim 3, wherein the power sensor is disposed at an angle to the longitudinal axis.

8. The apparatus recited in claim 1, wherein the housing includes cooling fins for dissipating thermal energy.

9. The apparatus recited in claim 1, wherein the power level of said attenuated output beam is reduced to approximately one twentieth the power level of the input beam.

10. The apparatus recited in claim 1, wherein said output beam is provided to an area of medical treatment.

11. A method for providing accurate delivery and measurement of low levels of laser power at the end of a laser guide comprising the steps of:
    providing laser energy at high power levels through the laser guide to the end of the guide;
    attenuating the laser energy at the end of the guide and providing an attenuated output beam;
    providing a reflected beam at the end of the guide, said energy in the reflected beam being related to the power level of the output beam, said step of attenuating comprising attenuating the input laser beam with a duel wavelength beam splitter which provides said attenuated output beam and further transmits a visible guide beam, said step of providing said reflected beam being further accomplished by said beam splitter;
    measuring the power level of the reflected beam, with a thermal energy sensor; and
    displaying the power level of the output beam based on the measurement of the power level of the reflected beam.

12. The method recited in claim 11, wherein said step of providing laser energy through the laser guide comprises providing the laser energy through an articulated arm laser guide.

13. The method recited in claim 11, further comprising disposing said beam splitter at an angle to the direction of said input beam such that a normal to the plane of the beam splitter is at an angle of less than 15° with respect to said direction.

14. The method recited in claim 13, wherein said angle is 12°.

15. The method recited in claim 11, wherein said step of displaying comprises displaying the power level of the output beam with a battery powered display device.

16. The method recited in claim 11, further comprising cooling said thermal energy sensor.

17. The method recited in claim 11, further comprising providing the output beam to an area of medical treatment.

18. The method recited in claim 11, further comprising the step of providing a visible guide beam through said dual wavelength beam splitter for guiding the placement of the attenuated output beam.

* * * * *